United States Patent [19]

Baumeister et al.

[11] Patent Number: 4,506,099
[45] Date of Patent: Mar. 19, 1985

[54] PROCESS FOR PRODUCING SUBSTITUTED 1,11-DIAMINOUNDECANES

[75] Inventors: Peter Baumeister, Fluh; Dieter Reinehr, Kandern; Eckehard Rosenegger, Riehen, all of Switzerland

[73] Assignee: Ciba-Geigy Corporation, Ardsley, N.Y.

[21] Appl. No.: 430,641

[22] Filed: Sep. 30, 1982

[30] Foreign Application Priority Data

Oct. 12, 1981 [CH] Switzerland ............... 6507/81

[51] Int. Cl.³ .................. C07C 85/00; C07C 85/20
[52] U.S. Cl. ..................... 564/413; 564/306; 564/316; 564/384; 564/391; 564/452; 564/453; 564/455; 564/487; 564/511; 549/492; 546/192; 546/246
[58] Field of Search ............. 564/452, 511, 413, 306, 564/316, 384, 391, 453; 549/492; 546/246, 192

[56] References Cited

U.S. PATENT DOCUMENTS 4,332,969 6/1982 Reinehr et al. ............... 564/452 X

Primary Examiner—Paul F. Shaver
Attorney, Agent, or Firm—Luther A. R. Hall

[57] ABSTRACT

Diamines of the formula I

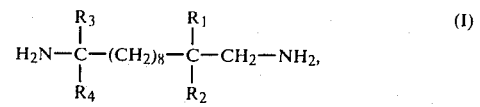

wherein $R_1$, $R_2$, $R_3$ and $R_4$ have the meanings defined in claim 1, can be produced by a simple process comprising reacting 1-aza-1,5,9-cyclododecatrienes, correspondingly substituted in the 3- and/or 12-position, with ammonia and hydrogen, in the presence of a hydrogenation catalyst, to obtain compounds (I). The compounds (I) are used for example as curing agents for epoxide resins, or for producing polyamides.

12 Claims, No Drawings

PROCESS FOR PRODUCING SUBSTITUTED 1,11-DIAMINOUNDECANES

The invention relates to a novel process for producing substituted 1,11-diaminoundecanes.

According to EP Publication No. 11599, 1,11-diaminoundecanes substituted in the 1,10-position can be produced by, inter alia, treating corresponding 1-aza-1,5,9-cyclododecatrienes or -dodecenes with an acid which is nonoxidising under the reaction conditions, such as HCl or sulfuric acid, and subsequently catalytically hydrogenating the treated product in the presence of liquid ammonia.

It is also known, from the German Offenlegungsschriften Nos. 2,048,750 and 2,824,423, that primary alkylamines or aliphatic or cycloaliphatic diamines can be obtained by reacting, in the first stage, corresponding aldehydes or dialdehydes with ammonia or monoamines to obtain Schiff bases, and converting these in the second reaction stage, at elevated temperatures and increased pressure, with ammonia and hydrogen, in the presence of hydrogenation catalysts, into the amines or diamines.

It has now been found that 1-aza-1,5,9-cyclododecatrienes of the type described in the German Offenlegungsschrift No. 2,831,353 and in the above-mentioned EP Publication or of a similar type, which in themselves are very stable compounds, can surprisingly be converted directly, that is to say, without the addition of acid, into substituted 1,11-diaminoundecanes. The contamination of waste water with salts, which is so undesirable from an ecological standpoint, is thus also avoided.

The invention relates therefore to a novel process for producing compounds of the formula I

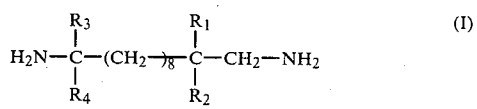

wherein
$R_1$ is $C_{1-12}$-alkyl,
$R_2$ is hydrogen or $C_{1-12}$-alkyl,
$R_3$ is $C_{1-12}$-alkyl, cycloalkyl having 4–12 ring C atoms, or unsubstituted or substituted phenyl, or piperidyl, tetrahydrofuryl or tetrahydrothienyl,
$R_4$ is hydrogen, $C_{1-12}$-alkyl, cycloalkyl having 4–12 ring C atoms, or unsubstituted or substituted phenyl, or
$R_1$ and $R_2$ and/or $R_3$ and $R_4$ together are alkylene having 3–11 C atoms, or $-CH_2-C(CH_3)_2-NH-C(CH_3)_2-CH_2-$,
by reacting a compound of the formula II

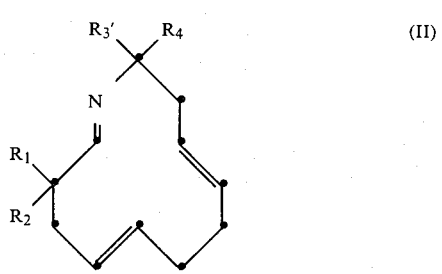

wherein $R_1$, $R_2$ and $R_4$ have the meanings defined under the formula I, and $R_3'$ is $C_{1-12}$-alkyl, cycloalkyl having 4–12 ring C atoms, or unsubstituted or substituted phenyl, or pyridyl, furyl or thienyl, or together with $R_4$ it is alkylene having 3–11 C atoms, or $-CH_2-C(CH_3)_2-NH-C(CH_3)_2-CH_2-$, with ammonia and hydrogen, in the presence of a hydrogenation catalyst, to obtain a compound of the formula I.

Alkyl groups denoted by $R_1$ to $R_4$ can be straight-chain or branched-chain. Alkyl groups $R_1$, $R_2$ and $R_4$ preferably have 1–5 C atoms and are straight-chain. Alkyl groups $R_3$ or $R_3'$ advantageously have 1–7 C atoms; particularly preferred are alkyl groups $R_3$ and $R_3'$ having 1–3 C atoms. Examples of alkyl groups $R_1$ to $R_4$ are: the methyl, ethyl, n-propyl, isopropyl, n-, sec- and tert-butyl, n-pentyl, 2- or 3-pentyl, n-hexyl, 2- or 3-heptyl, n-octyl, n-decyl and n-dodecyl groups.

Cycloalkyl groups $R_3$, $R_3'$ and $R_4$ can be unsubstituted, or substituted by $C_{1-4}$-alkyl groups. They are especially cycloalkyl groups substituted by a methyl or ethyl group. Preferably, however, cycloalkyl groups $R_3$, $R_3'$ and $R_4$ are unsubstituted and have 5–8 ring C atoms. Particularly preferred are the cyclopentyl group and above all the cyclohexyl group.

When $R_3$, $R_3'$ or $R_4$ is substituted phenyl, suitable as substituents are in particular alkyl groups having 1–4 C atoms and especially 1 or 2 C atoms. Phenyl groups $R_3$, $R_3'$ or $R_4$ can carry several alkyl groups; they are however preferably substituted by only one alkyl group. Phenyl which is unsubstituted is preferred.

Pyridyl, furyl or thienyl groups $R_3'$ are in particular the pyridyl-3, pyridyl-4, furyl-2 and thienyl-2 groups. These $R_3'$ groups are hydrogenated, during the reaction according to the invention, to the corresponding piperidyl, tetrahydrofuryl and tetrahydrothienyl groups.

Alkylene groups denoted by $R_1$ and $R_2$ and/or $R_3$ and $R_4$ together preferably have 4–7 C atoms. They are especially the tetramethylene and, more especially, the pentamethyl groups.

Preferred is the production of compounds of the formula I wherein $R_1$ is alkyl having 1–5 C atoms, $R_2$ is hydrogen or alkyl having 1–5 C atoms, $R_3$ is alkyl having 1–7 C atoms, cycloalkyl having 5–8 C atoms, especially cyclohexyl, phenyl, tetrahydrofuryl or piperidyl, and $R_4$ is hydrogen or alkyl having 1–5 C atoms, or $R_3$ and $R_4$ together are alkylene having 4–7 C atoms or $-CH_2-C(CH_3)_2-NH-C(CH_3)_2-CH_2-$.

Particularly preferred is the production of compounds of the formula I wherein $R_1$ is alkyl having 1–5 C atoms, $R_2$ is alkyl having 1–5 C atoms or hydrogen, $R_3$ is alkyl having 1–5 C atoms, phenyl, 2-tetrahydrofuryl or 3-piperidyl, and $R_4$ is hydrogen or methyl, or $R_3$ and $R_4$ together are $-(CH_2)_4-$, $-(CH_2)_5-$ or $-CH_2-C(CH_3)_2-NH-C(CH_3)_2-CH_2-$. More especially preferred is the production of compounds of the formula I wherein $R_1$ is methyl or ethyl, $R_2$ is hydrogen, methyl or ethyl, $R_3$ is alkyl having 1–3 C atoms, particularly isopropyl, or phenyl, and $R_4$ is hydrogen or methyl, or $R_3$ and $R_4$ together are $-(CH_2)_5$.

Anhydrous ammonia or aqueous or aqueous-organic ammonia solutions can be used for the reaction according to the invention. Suitable inert organic solvents are for example: alcohols having up to 6 C atoms, such as methanol, ethanol, isopropanol, butanols, pentanols and hexanols; and ethers, particularly cyclic ethers, such as tetrahydrofuran and dioxane; also hydrocarbons, for example cyclohexane.

Aqueous ammonia solutions are preferably used, especially 20–30% aqueous ammonia solutions.

The hydrogenation catalysts used can be compounds known per se, such as platinum, rhodium, palladium ruthenium, nickel or cobalt and iron catalysts. Ruthenium and nickel catalysts are preferred, especially Raney nickel, nickel on kieselguhr and ruthenium on charcoal. More particularly preferred is ruthenium on charcoal.

The catalysts are advantageously used in amounts of 0.1 to 50% by weight, preferably 0.5 to 25% by weight, relative to the compound of the formula II.

The reaction temperatures are in general between 20° and 300° C., preferably between 100° and 250° C. The hydrogen pressure is advantageously between 10 and 400 bar, in particular between 20 and 100 bar.

The compounds of the formula II and the ammonia are advantageously used in a molar ratio of 1:1 to 1:50, preferably 1:1 to 1:20. The compounds of the formula II are known, or they can be produced by the process described in the German Offenlegungsschrift No. 2,831,353.

After completion of the reaction, the compounds of the formula I can be purified in the customary manner, for example by means of distillation.

The compounds of the formula I are used as curing agents for epoxide resins, or for producing transparent polyamides, cp., EP Publication No. 11599.

EXAMPLE 1

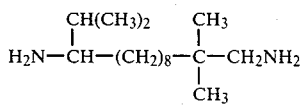

830 g of a 25% aqueous ammonia solution (about 12.2 mols of $NH_3$) are placed together with 80 g of Raney nickel into a 2.5 liter autoclave with magnetic stirrer. After the autoclave has been heated to 180° C., hydrogen is injected up to a total pressure of 100 bar. There are then introduced in controlled amounts by means of a dosing pump, in the course of one hour, 208 g (0.89 mol) of 3,3-dimethyl-12-isopropyl-1-aza-1,5,9-cyclododecatriene (ratio of 1-aza-1,5,9-cyclododecatriene to ammonia=1:13.7). The reaction mixture is reacted for 9 hours, and is subsequently cooled and distilled. After first runnings of 10.2 g, the yield is 199 g (0.776 mol) of 1-isopropyl-10,10-dimethyl-1,11-diaminoundecane (corresponding to 87% of theory); b.p. 87°–89° C./4 Pa.

EXAMPLE 2

By using in Example 1 80 g of nickel on kieselguhr (55% Ni) instead of 80 g of Raney nickel, under otherwise the same reaction conditions, there is obtained 1-isopropyl-10,10-dimethyl-1,11-diaminoundecane in a yield of 88.5% of theory.

EXAMPLE 3

The procedure is carried out in the manner described in Example 1 except that there are used 52.2 g (0.225 mol) of 3,3-dimethyl-12-isopropyl-1-aza-1,5,9-cyclododecatriene, 20 g of Raney nickel and 75 g (1.1 mol) of a 25% aqueous ammonia solution (ratio of 1-aza-1,5,9-cyclododecatriene to ammonia=1:4.9). After a reaction time of 9 hours at 175° C. and a hydrogen pressure of 100 bar, the yield on subsequent distillation is 49 g (0.192 mol) of 1-isopropyl-10,10-dimethyl-1,11-diaminoundecane, corresponding to 85% of theory.

EXAMPLE 4

The procedure is carried out in the manner described in Example 1 but with the use of 26.1 g (0.112 mol) of 3,3-dimethyl-12-isopropyl-1-aza-1,5,9-cyclodecatriene, 5 g of Raney nickel and 105 g (1.55 mols) of a 25% aqueous ammonia solution. After a reaction time of 9 hours at 195°–200° C. with a hydrogen pressure of 100 bar, there are obtained after distillation 25 g (0.0975 mol) of 1-isopropyl-10,10-dimethyl-1,11-diaminoundecane in a yield of 87% of theory.

EXAMPLE 5

The procedure is carried out as described in Example 4 except that the reaction time is reduced from 9 to 3.5 hours. 1-Isopropyl-10,10-dimethyl-1,11-diaminoundecane is obtained in a yield of 86% of theory.

EXAMPLE 6

The procedure is carried out in the manner described in Example 1 but with the use of 197 g (0.9 mol) of 3,3-dimethyl-12-ethyl-1-aza-1,5,9-cyclododecatriene in place of 208 g of 3,3-dimethyl-12-isopropyl-1-aza-1,5,9-cyclododecatriene. The result after distillation is 194 g (0.8 mol) of 1-ethyl-10,10-dimethyl-1,11-diaminoundecane in a yield of 89% of theory; b.p. 85°–87° C./4 Pa.

EXAMPLE 7

The procedure is carried out in the manner described in Example 1 but with the use of 228 g (0.9 mol) of 3-methyl-12-phenyl-1-aza-1,5,9-cyclododecatriene in place of 208 g (0.89 mol) of 3,3-dimethyl-12-isopropyl-1-aza-1,5,9-cyclododecatriene. There are obtained after distillation 210 g (0.76 mol) of 1-phenyl-10-methyl-1,11-diaminoundecane in a yield of 84.5% of theory; b.p. 137°–140° C./1 Pa.

EXAMPLES 8–26

75 g of a 25% aqueous ammonia solution are placed together with 10 g of Raney nickel and 20 ml of 1N aqueous NaOH as well as 52.2 g (0.2 mol) of 3,3-dimethyl-12-isopropyl-1-aza-1,5,9-cyclododecatriene into an autoclave with magnetic stirrer. After the reaction mixture has been heated to 175° C., hydrogen gas is injected up to a total pressure of 50 bar. After a reaction time of 9 hours, the mixture is cooled and distilled. There is obtained 65% of the theoretical yield of 1-isopropyl-10,10-dimethyl-1,11-diaminoundecane.

1-Isopropyl-10,10-dimethyl-1,11-diaminoundecane is produced in an analogous manner under the reaction conditions given in the following Table I.

TABLE I

| Example No. | Catalyst | Additive | Time | Temp. °C. | Pressure | Yield % of theory |
|---|---|---|---|---|---|---|
| 9 | 5 g of Ru/C 5% | 20 ml of 1N NaOH | 2,5 h | 180 | 50 bar | 95 |
| 10 | 20 g of Ra—Ni | — | 17 h | 180 | 50 bar | 97 |
| 11 | 10 g of Ra—Ni | — | 48 h | 180 | 100 bar | 90 |
| 12 | 10 g of Ra—Ni | — | 6 h | 180 | 50 bar | 10 |
| 13 | 10 g of Ra—Ni | — | 23 h | 180 | 50 bar | 80 |
| 14 | 10 g of Ra—Ni | 2 ml of 1N NaOH | 20,5 h | 180 | 50 bar | 60 |
| 15 | 2.5 g of Ru/C | 2 ml | 0,75 h | 180 | 50 bar | 95 |

TABLE I-continued

| Example No. | Catalyst | Additive | Time | Temp. °C. | Pressure | Yield % of theory |
|---|---|---|---|---|---|---|
| 16 | 1.3 g of Pd/C 5% | 2 ml of 1N NaOH | 44 h | 180 | 50 bar | 15 |
| 17 | 10 g of Ra—Ni | 1.6 g of NaOAc | 28 h | 180 | 50 bar | 70 |
| 18 | 10 g of Ra—Ni | — | 15 h | 200 | 50 bar | 60 |
| 19 | 10 g of Ra—Ni | — | 42 h | 180 | 35 bar | 80 |
| 20 | 10 g of Ra—Ni | 2 g of NEt$_3$ | 22 h | 180 | 50 bar | 70 |
| 21 | 10 g of Ra—Co | — | 43 h | 180 | 100 bar | 40 |
| 22 | 10 g of Ra—Fe | — | 70 h | 200 | 100 bar | 20 |
| 23a | 1.2 g of Ru/C 10% | 2 ml of 1N NaOH | 14,5 h | 125-30 | 50 bar | 90 |
| b | | | 10 h | 125-30 | 20 bar | 90 |
| 24 | 10 g of Ra—Cu | — | 54 | 175-180 | 50 bar | 40 |
| 25 | 5 g of Pt/C 5% | — | 0,5 h | 175-180 | 50 bar | 10 |
| 26 | 5 g of Rh/Al$_2$O$_3$ 5% | — | 23 h | 175-180 | 50 bar | 30 |

EXAMPLES 27-32

In each case, 0.1 mol of a compound of the formula II, which is a starting material for producing a compound of the formula I having the meanings for $R_1$ to $R_4$ given in Table II, together with 42.5 g of a 25% aqueous ammonia solution and 1.25 g of a ruthenium on active charcoal hydrogenation catalyst (10% Ru) are placed into an autoclave with magnetic stirrer. After the reaction mixture has been heated, hydrogen gas is injected up to a total pressure of 50 bar. When no further fall in pressure occurs, the mixture is cooled and the diamine is separated by distillation. The reaction times and results are summarised in Table II.

TABLE II

| Example No. | Diamine of the formula I | | | | Reaction time | $n_D^{20}$ | Yield % of theory |
|---|---|---|---|---|---|---|---|
| | $R_1$ | $R_2$ | $R_3$ | $R_4$ | | | |
| 27 | CH$_3$ | CH$_3$ | C$_2$H$_5$ | H | 2,5 h | 1,4622 | 75 |
| 28 | CH$_3$ | H | CH$_3$ | CH$_3$ | 28 h | 1,4585 | 40 |
| 29 | CH$_3$ | CH$_3$ | ⋇ | | 19,5 h | 1,4887 | 75 |
| 30 | CH$_3$ | H | C$_6$H$_5$ | H | 22 h | 1,5095 | 60 |
| 31 | C$_2$H$_5$ | C$_2$H$_5$ | iC$_3$H$_7$ | H | 16 h | 1,4704 | 50 |
| 32 | C$_2$H$_5$ | H | —(CH$_2$)$_5$— | | 6 h | 1,4815 | 80 |

*The corresponding starting product of the formula II can be produced as follows:

400 g of 2-methylallylamine are dissolved in 400 ml of toluene in a 2.5 liter sulfonating flask, and 450 g of microfilter are added. A solution of 700 g of 2,2,6,6-tetramethyl-4-piperidone in 300 ml of toluene is then added dropwise in such a manner that the reaction temperature is kept at 30°-35° C. After the addition is completed, stirring is maintained for 6 hours at room temperature. The mixture is filtered off from the microfilter, and the solvent is removed in a rotary evaporator. Distillation of the residue yields 778 g of N-(2,2,6,6-tetramethyl-4-piperidylidene)-2-methylallylamine, corresponding to 83% of theory, in the form of a colourless liquid having a boiling point of 63° C. at 40 Pa.

162.5 g of the N-(2,2,6,6-tetramethyl-4-piperidylidene)-2-methylallylamine are dissolved in 162 ml of toluene in a 500 ml three-necked flask with reflux condenser, and 4.86 g of potassium tert-butylate are added. To the reaction mixture are then added, with stirring, 50 ml of dimethyl sulfoxide, and stirring is maintained at 50° C. for 8 hours. The organic phase is afterwards extracted with 100 ml of distilled water, and the organic part, after separation of the solvent, is distilled to yield 136.9 g of N-(2,2,6,6-tetramethyl-4-piperidylidene)-2-methyl-1-amino-1-propene as a colourless liquid, b.p. 56° C. at 40 Pa (82% of theory).

136.0 g of the N-(2,2,6,6-tetramethyl-4-piperidylidene)-2-methyl-1-amino-1-propene, 3.9 g of nickel acetylacetonate and 1.85 g of trimethyl phosphite are dissolved in 150 ml of toluene under argon in a 500 ml Schlenk ampoule, and 5.5 ml of ethoxydiethylaluminium are added. There are subsequently incorporated by condensation 86 g of 1,3-butadiene at −78° C., and the mixture is warmed to room temperature with stirring. The mixture after 1 hour is heated to 40° C. and is stirred for 18 hours at this temperature. After the cooling of the mixture and separation of the solvent, the mixture is distilled to thus obtain 106.8 g of 12-spiro-(2,2,6,6-tetramethyl-4-piperidyl)-3,3-dimethyl-1-aza-1,5,9-cyclododecatriene as colourless oil, b.p. 136° C. at 40 Pa (51.6% of theory).

EXAMPLE 33

Example 27 is repeated but with the use of 24.35 g (0.1 mol) of 12-(2-furyl)-3-methyl-1-aza-1,5,9-cyclododecatriene. The yield after distillation is 80% of theory of 1-(2-tetrahydrofuryl)-10-methyl-1,11-diaminoundecane; $n_D^{20}$: 1.4800.

EXAMPLE 34

Example 27 is repeated but with the use of 25.4 g (0.1 mol) of 12-(3-pyridyl)-3-methyl-1-aza-1,5,9-cyclododecatriene. The yield after a reaction time of 33 hours and after processing is 45% of theory of 1-(3-piperidino)-10-methyl-1,11-diaminoundecane; $n_D^{20}$:1.4762.

EXAMPLE 35

0.25 mol of 3,3-dimethyl-12-isopropyl-1-aza-1,5,9-cyclododecatriene together with 85 ml of 25% aqueous ammonia solution and 1.5 g of a rhutenium on active charcoal hydrogenation catalyst (10% Ru) are placed into the reaction vessel and are heated to 180° C. under a hydrogen pressure of 50 bar. No further H$_2$ absorption can be detected after a reaction time of 30 minutes. Further processing by distillation of the filtered reaction mixture yields the product in a yield of 90% of theory.

APPLICATION EXAMPLE (i) 0.1 mol of terephthalic acid in 300 ml of 70% ethanol are brought to boiling in a round-bottomed flask fitted with stirrer, reflux condenser and dropping funnel. Into the boiling suspension is introduced dropwise from the dropping funnel in the course of about 10 minutes, with stirring, 0.1 mol of 1-isopropyl-10,10-dimethyl-1,11-diaminoundecane, and diamine residues adhering in the funnel are rinsed quantitatively with an amount of ethanol into the reaction mixture. The formed clear solution is allowed to cool with continuous stirring; the salt which precipitates is filtered off and then dried at 90° C. in vacuo.

(ii) The following components are weighed into a bomb tube which is provided with a screw cap with incorporated relief pressure valve:

(a) 4,4′-diamino-3,3′-dimethyldicyclohexylmethane,
(b) an amount of isophthalic acid equivalent to this diamine,
(c) 70% by weight, relative to the total weight of reaction components, of the salt obtained according to (i).

After the air in the bomb tube has been completely expelled by nitrogen or by some other inert gas, the bomb tube is closed and is immersed in a salt bath of which the temperature is 270° C. A homogeneous transparent melt has formed after 30 to 60 minutes. After a total of 3 hours, the precondensation is terminated by removing the bomb tube from the salt bath, and releasing the excess pressure by opening the valve. The solidified transparent precondensate is taken from the bomb tube and transferred to a condensation vessel. With the strict exclusion of air and with the continuous passing through of nitrogen, the melt is polycondensed for 5 hours at a salt-bath temperature of 280° C., in the course of which the reaction water is continuously removed by the flow of nitrogen. The melt on cooling solidifies to form a transparent substance. An amount of 2-3 g of the produced copolyamide is moulded in a heatable hydraulic press at 270° C. into the form of a sheet about 0.4 to 1 mm thick. The copolyamide obtained has a reduced specific viscosity $\eta$ red. of 1.09 dl/g, measured on a 0.5% solution in m-cresol at 25° C., and a glass transition temperature of 162° C. (measured in a differential calorimeter, DSC). The copolymide also has very good resistance to boiling water, that is to say, there is no impairment of the transparency even after several days.

What is claimed is:

1. A process for producing a compound of the formula I

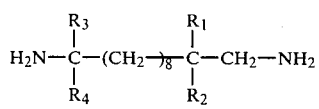

wherein
$R_1$ is $C_{1-12}$-alkyl,
$R_2$ is hydrogen or $C_{1-12}$-alkyl,
$R_3$ is $C_{1-12}$-alkyl, cycloalkyl having 4-12 ring C atoms, or unsubstituted or substituted phenyl, or piperidyl, tetrahydrofuryl or tetrahydrothienyl,
$R_4$ is hydrogen, $C_{1-12}$-alkyl, cycloalkyl having 4-12 ring C atoms, or unsubstituted or substituted phenyl, or
$R_1$ and $R_2$ and/or $R_3$ and $R_4$ together are alkylene having 3-11 C atoms, or —CH$_2$—C(CH$_3$)$_2$—NH—C(CH$_3$)$_2$—CH$_2$—, which comprises reacting a compound of the formula II

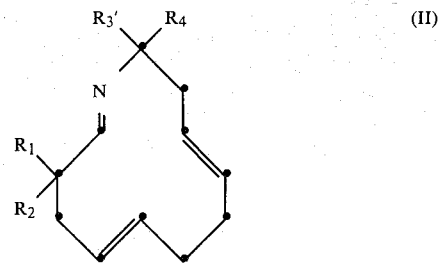

wherein $R_1$, $R_2$ and $R_4$ have the meanings defined under the formula I, and $R_3'$ is $C_{1-12}$-alkyl, cycloalkyl having 4-12 ring C atoms, or unsubstituted or substituted phenyl, or pyridyl, furyl or thienyl, or together with $R_4$ it is alkylene having 3-11 C atoms, or —CH$_2$—C(CH$_3$)$_2$—NH—C(CH$_3$)$_2$—CH$_2$—, with ammonia and hydrogen, in the presence of a hydrogenation catalyst, to obtain a compound of the formula I.

2. A process according to claim 1, wherein there is produced a compound of the formula I in which $R_1$ is alkyl having 1-5 C atoms, $R_2$ is hydrogen or alkyl having 1-5 C atoms, $R_3$ is alkyl having 1-7 C atoms, cycloalkyl having 5-8 C atoms, phenyl, tetrahydrofuryl or piperidyl, and $R_4$ is hydrogen or alkyl having 1-5 C atoms, or $R_3$ and $R_4$ together are alkylene having 4-7 C atoms or —CH$_2$—C(CH$_3$)$_2$—NH—C(CH$_3$)$_2$—CH$_2$—.

3. A process according to claim 1, wherein there is used a compound of the formula I in which $R_1$ is alkyl having 1-5 C atoms, $R_2$ is alkyl having 1-5 C atoms or hydrogen, $R_3$ is alkyl having 1-5 C atoms, phenyl, 2-tetrahydrofuryl or 3-piperidyl, and $R_4$ is hydrogen or methyl, or $R_3$ and $R_4$ together are —(CH$_2$)$_4$—, —(CH$_2$)$_5$— or —CH$_2$—C(CH$_3$)$_2$—NH—C(CH$_3$)$_2$—CH$_2$—.

4. A process according to claim 1, wherein there is produced a compound of the formula I in which $R_1$ is methyl or ethyl, $R_2$ is hydrogen, methyl or ethyl, $R_3$ is alkyl having 1-3 C atoms, or phenyl, and $R_4$ is hydrogen or methyl, or $R_3$ and $R_4$ together are —(CH$_2$)$_5$—.

5. A process according to claim 1, wherein the reaction is performed in aqueous ammonia.

6. A process according to claim 1, wherein the catalyst used is Raney nickel, nickel on kieselguhr or ruthenium on charcoal.

7. A process according to claim 1, wherein the reaction is performed at a temperature of between 100° and 250° C.

8. A process according to claim 1, wherein the reaction is performed at a pressure of between 20 and 100 bar.

9. A process according to claim 1, wherein the catalyst is used in an amount of 0.5 to 25% by weight, relative to the compound of the formula II.

10. A process according to claim 2 wherein $R_3$ is cyclohexyl.

11. A process according to claim 4 wherein $R_3$ is isopropyl.

12. A process according to claim 6 wherein the catalyst is ruthenium on charcoal.

* * * * *